United States Patent
Möller et al.

(10) Patent No.: US 7,122,657 B2
(45) Date of Patent: Oct. 17, 2006

(54) UDP-GLUCOSE AGLYCON-GLUCOSYTRANSFERASE

(76) Inventors: Birger Lindberg Möller, Kongstedvej 5, 2700 Brönshöj (DK); Peter Höj, 14 The Parkway, 5068 Leabrook, S.A. (AU); Patrik Raymond Jones, c/o Yumi Otani, 4-5-16 cs coupo No. 201 Omote Chou, Sakura-Shi, 285 Chiba (JP)

( * ) Notice: Subject to any disclaimer, the term of this patent is extended or adjusted under 35 U.S.C. 154(b) by 251 days.

(21) Appl. No.: 10/148,606
(22) PCT Filed: Nov. 29, 2000
(86) PCT No.: PCT/EP00/11982

§ 371 (c)(1),
(2), (4) Date: Jul. 15, 2002

(87) PCT Pub. No.: WO01/40491
PCT Pub. Date: Jun. 7, 2001

(65) Prior Publication Data
US 2005/0277766 A1   Dec. 15, 2005

(30) Foreign Application Priority Data
Dec. 1, 1999  (EP) .................................. 99123838

(51) Int. Cl.
C12N 15/29 (2006.01)
C12N 15/52 (2006.01)
C12N 15/82 (2006.01)
A01H 5/00 (2006.01)
A01H 5/10 (2006.01)

(52) U.S. Cl. .................. 536/23.6; 536/23.1; 536/23.2; 536/24.3; 435/320.1; 435/419; 435/468

(58) Field of Classification Search .............. 536/23.1, 536/23.2, 23.6, 24.3; 800/278, 279, 283, 800/298, 320, 320.1; 435/320.1, 419, 468
See application file for complete search history.

(56) References Cited

FOREIGN PATENT DOCUMENTS

| WO | WO 95 16041 | 6/1995 |
|---|---|---|
| WO | WO 98 40470 | 9/1998 |
| WO | WO 01 40491 A3 | 6/2001 |

OTHER PUBLICATIONS

Hughes J. et al. DNA sequence, 1994; vol. 5, pp. 41-49.*
Jones P. R. et al. Journal of Biological Chemistry, Dec. 10, 1999; vol. 274, No. 50, pp. 35483-35491.*
Ralston E. J. et al. Genetics, May 1988; vol. 119, pp. 185-197.*
Fraissinet-Tachet L. et al. FEBS Letters, 1998; vol. 437, pp. 319-323.*
Ford C. M. et al. Journal of Biological Chemistry, Apr. 10, 1998, vol. 273 No. 15 pp. 9224-9233.*
Hughes, J. and Hughes, M., *Multiple Secondary Plant Product UDP-glucose glucosyltransferase genes expressed in cassava (Manihot esculenta Crantz) cotyledons DNA Sequence*, vol. 5, (1994) pp. 41-49.
Jones et al., *The UDP-glucose: p-hydroxymandelonitrile-O-glucosyltransferase that catalyzes the last step in synthesis of the cyanogenic glucoside dhurrin in Sorghum bicolor Journal of Biological Chemistry*, vol. 274, No. 50 (Dec. 10, 1999), pp. 35483-35491.
Reay, P.F. and Conn, E., *The Purification and Properties of a Uridine Diphosphate Glucose: Aldehyde Cyanohydrin β-Glucosyltransferase from Sorghum Seedlings Journal of Biological Chemistry*, vol. 249, No. 18 (Sep. 25, 1974) pp. 5826-5830.

* cited by examiner

Primary Examiner—Russell P. Kallis

(57) ABSTRACT

The present invention provides DNA molecules coding for a UDP-glucose:alycon-glucosyltransferase conjugating cyanohydrins, terpenoids, phenylderivatives or hexanolderivatives to glucose. Trangenic expression of corresponding genes in plants can be used to influence the biosynthesis of the corresponding glucosides.

15 Claims, No Drawings

SEQUENCE LISTING

<160> NUMBER OF SEQ ID NOS: 9

<210> SEQ ID NO 1
<211> LENGTH: 492
<212> TYPE: PRT
<213> ORGANISM: Sorghum bicolor

<400> SEQUENCE: 1

```
Met Gly Ser Asn Ala Pro Pro Pro Thr Pro His Val Val Leu Val
1               5                   10                  15

Pro Phe Pro Gly Gln Gly His Val Ala Pro Leu Met Gln Leu Ala Arg
                20                  25                  30

Leu Leu His Ala Arg Gly Ala Arg Val Thr Phe Val Tyr Thr Gln Tyr
            35                  40                  45

Asn Tyr Arg Arg Leu Leu Arg Ala Lys Gly Glu Ala Ala Val Arg Pro
    50                  55                  60

Pro Ala Thr Ser Ser Ala Arg Phe Arg Ile Glu Val Ile Asp Asp Gly
65                  70                  75                  80

Leu Ser Leu Ser Val Pro Gln Asn Asp Val Gly Gly Leu Val Asp Ser
                85                  90                  95

Leu Arg Lys Asn Cys Leu His Pro Phe Arg Ala Leu Leu Arg Arg Leu
            100                 105                 110

Gly Gln Glu Val Glu Gly Gln Asp Ala Pro Pro Val Thr Cys Val Val
        115                 120                 125

Gly Asp Val Val Met Thr Phe Ala Ala Ala Ala Arg Glu Ala Gly
    130                 135                 140

Ile Pro Glu Val Gln Phe Phe Thr Ala Ser Ala Cys Gly Leu Leu Gly
145                 150                 155                 160

Tyr Leu His Tyr Gly Glu Leu Val Glu Arg Gly Leu Val Pro Phe Arg
                165                 170                 175

Asp Ala Ser Leu Leu Ala Asp Asp Tyr Leu Asp Thr Pro Leu Glu
            180                 185                 190

Trp Val Pro Gly Met Ser His Met Arg Leu Arg Asp Met Pro Thr Phe
        195                 200                 205

Cys Arg Thr Thr Asp Pro Asp Asp Val Met Val Ser Ala Thr Leu Gln
    210                 215                 220

Gln Met Glu Ser Ala Ala Gly Ser Lys Ala Leu Ile Leu Asn Thr Leu
225                 230                 235                 240

Tyr Glu Leu Glu Lys Asp Val Val Asp Ala Leu Ala Ala Phe Phe Pro
                245                 250                 255
```

```
Pro Ile Tyr Thr Val Gly Pro Leu Ala Glu Val Ile Ala Ser Ser Asp
            260                 265                 270

Ser Ala Ser Ala Gly Leu Ala Ala Met Asp Ile Ser Ile Trp Gln Glu
            275                 280                 285

Asp Thr Arg Cys Leu Ser Trp Leu Asp Gly Lys Pro Ala Gly Ser Val
            290                 295                 300

Val Tyr Val Asn Phe Gly Ser Met Ala Val Met Thr Ala Ala Gln Ala
305                 310                 315                 320

Arg Glu Phe Ala Leu Gly Leu Ala Ser Cys Gly Ser Pro Phe Leu Trp
                325                 330                 335

Val Lys Arg Pro Asp Val Val Glu Gly Glu Val Leu Leu Pro Glu
            340                 345                 350

Ala Leu Leu Asp Glu Val Ala Arg Gly Arg Gly Leu Val Val Pro Trp
            355                 360                 365

Cys Pro Gln Ala Ala Val Leu Lys His Ala Ala Val Gly Leu Phe Val
            370                 375                 380

Ser His Cys Gly Trp Asn Ser Leu Leu Glu Ala Thr Ala Ala Gly Gln
385                 390                 395                 400

Pro Val Leu Ala Trp Pro Cys His Gly Glu Gln Thr Thr Asn Cys Arg
                405                 410                 415

Gln Leu Cys Glu Val Trp Gly Asn Gly Ala Gln Leu Pro Arg Glu Val
            420                 425                 430

Glu Ser Gly Ala Val Ala Arg Leu Val Arg Glu Met Met Val Gly Asp
            435                 440                 445

Leu Gly Lys Glu Lys Arg Ala Lys Ala Glu Trp Lys Ala Ala Ala
            450                 455                 460

Glu Ala Ala Ala Arg Lys Gly Gly Ala Ser Trp Arg Asn Val Glu Arg
465                 470                 475                 480

Val Val Asn Asp Leu Leu Leu Val Gly Gly Lys Gln
                485                 490

<210> SEQ ID NO 2
<211> LENGTH: 1479
<212> TYPE: DNA
<213> ORGANISM: Sorghum bicolor

<400> SEQUENCE: 2
atgggcagca acgcgccgcc tccgccgacg cctcacgtgg tgctggtccc gttcccgggg      60
cagggccacg tcgcgccgct gatgcagctg gcgcgcctcc tccacgcccg ggcgcgcgc     120 gtcaccttcg tctacaccca gtacaactac cgccgcctcc tgcgcgccaa gggcgaggcc     180
gccgtcaggc cccccgccac ctcctccgcg aggttccgca tcgaggtcat cgacgacggc     240 ctctcccttct ccgtgccgca gaacgacgtc gggggggctcg tcgactccct gcgcaaaaac     300
tgcctccacc cgttccgcgc cctgctcgcg cgcctggggc aggaggtgga ggggcaagac     360
gcgccgcccg tcacctgcgt cgtcggcgac gtcgtcatga ccttcgccgc cgcagctgcc     420
agggaggccg gcatccccga ggtgcagttc ttcacggcct cagcatgcgg actcttgggc     480
tacttgcact acggcgagct cgtcgaacga ggcctcgtcc ctttcagaga cgccagcctc     540
ctcgccgacg acgattacct ggacacgccc ctggagtggg tgcccgggat gagccacatg     600
cggctcaggg acatgccgac gttctgccgc accacgggacc ccgacgacgt catggtgtcc     660
gccacgctcc agcagatgga gagcgccgcc ggctccaagg ccctcatcct caacaccctg     720
tacgagctcg agaaggacgt ggtggacgcg ctcgccgcct tcttcccgcc gatctacacc     780
```

-continued

```
gtggggccgc tcgccgaggt catcgcgtcc tccgactccg cctccgccgg cctcgccgcc    840
atggacatca gcatctggca ggaggacacg cggtgcctgt cgtggctcga cgggaagccg    900
gccggctccg tggtgtacgt caacttcggc agcatggccg tcatgacggc cgcgcaggcg    960
cgggagttcg cgctgggcct ggcaagctgc ggctccccgt tcctgtgggt gaagcgcccc   1020
gacgtggtgg aaggcgagga ggtgctgctg ccggaggccc tgctggacga ggtggctcgc   1080
ggcaggggcc tcgtggtgcc atggtgcccg caggcagcag tgctcaagca cgccgccgtg   1140
ggactgttcg tctcgcactg cggatggaac tccctgctgg aggcgacggc ggcggggcag   1200
ccggtgctcg cctggccctg ccacggggaa cagaccacca actgcaggca gctgtgcgag   1260
gtctggggca acggcgcgca gctgcccaga gaagtggaga gcggcgcggt ggcccgtctg   1320
gtgagggaga tgatggtcgg ggacctgggc aaggagaagc gggcgaaggc ggcggagtgg   1380
aaggcggcgg cggaggccgc ggccaggaaa ggcggcgcgt cgtggcgtaa tgttgaacgc   1440
gtggtgaacg acctgctgct ggtcgggggc aagcagtga                          1479
```

```
<210> SEQ ID NO 3
<211> LENGTH: 23
<212> TYPE: DNA
<213> ORGANISM: Artificial Sequence
<220> FEATURE:
<221> NAME/KEY: misc_feature
<223> OTHER INFORMATION: Primer C2EF
<220> FEATURE:
<221> NAME/KEY: modified_base
<222> LOCATION: (6)..(6)
<223> OTHER INFORMATION: i
<220> FEATURE:
<221> NAME/KEY: modified_base
<222> LOCATION: (9)..(9)
<223> OTHER INFORMATION: i
<220> FEATURE:
<221> NAME/KEY: modified_base
<222> LOCATION: (18)..(18)
<223> OTHER INFORMATION: i

<400> SEQUENCE: 3
ttygtnwsnc aytgyggntg gaa                                            23

<210> SEQ ID NO 4
<211> LENGTH: 17
<212> TYPE: DNA
<213> ORGANISM: Artificial Sequence
<220> FEATURE:
<221> NAME/KEY: misc_feature
<223> OTHER INFORMATION: T7 Primer

<400> SEQUENCE: 4
aatacgactc actatag                                                   17

<210> SEQ ID NO 5
<211> LENGTH: 23
<212> TYPE: DNA
<213> ORGANISM: Artificial Sequence
<220> FEATURE:
<221> NAME/KEY: misc_feature
<223> OTHER INFORMATION: Primer C2DF
<220> FEATURE:
<221> NAME/KEY: modified_base
<222> LOCATION: (6)..(6)
<223> OTHER INFORMATION: i
<220> FEATURE:
<221> NAME/KEY: modified_base
<222> LOCATION: (9)..(9)
<223> OTHER INFORMATION: i
<220> FEATURE:
```

```
<221> NAME/KEY: modified_base
<222> LOCATION: (12)..(12)
<223> OTHER INFORMATION: i
<220> FEATURE:
<221> NAME/KEY: modified_base
<222> LOCATION: (15)..(15)
<223> OTHER INFORMATION: i
<220> FEATURE:
<221> NAME/KEY: modified_base
<222> LOCATION: (18)..(18)
<223> OTHER INFORMATION: i

<400> SEQUENCE: 5
gargcnacng cngcnggnca rcc                                              23

<210> SEQ ID NO 6
<211> LENGTH: 21
<212> TYPE: DNA
<213> ORGANISM: Artificial Sequence
<220> FEATURE:
<221> NAME/KEY: misc_feature
<223> OTHER INFORMATION: Primer 441F

<400> SEQUENCE: 6
gaggcgacgg cggcggggca g                                                21

<210> SEQ ID NO 7
<211> LENGTH: 24
<212> TYPE: DNA
<213> ORGANISM: Artificial Sequence
<220> FEATURE:
<221> NAME/KEY: misc_feature
<223> OTHER INFORMATION: Primer 442R

<400> SEQUENCE: 7
catgtcactg cttgccccg acca                                              24

<210> SEQ ID NO 8
<211> LENGTH: 35
<212> TYPE: DNA
<213> ORGANISM: Artificial Sequence
<220> FEATURE:
<221> NAME/KEY: misc_feature
<223> OTHER INFORMATION: Primer EXF1

<400> SEQUENCE: 8
aataaaagca tatgggaagc aacgcgccgc ctccg                                 35

<210> SEQ ID NO 9
<211> LENGTH: 28
<212> TYPE: DNA
<213> ORGANISM: Artificial Sequence
<220> FEATURE:
<221> NAME/KEY: misc_feature
<223> OTHER INFORMATION: Primer EXR1

<400> SEQUENCE: 9
ttggatcctc actgcttgcc cccgacca                                         28
```

UDP-GLUCOSE AGLYCON-GLUCOSYTRANSFERASE

This is a § 371 of PCT/EP00/11982, filed Nov. 29, 2000, and published Jun. 7, 2001, as WO 01/40491, which claims priority of European Patent Application No. 99123838.7, filed Dec. 1, 1999.

The present invention provides DNA molecules coding for a UDP-glucose:aglycon-glucosyltransferase conjugating cyanohydrins, terpenoids, phenylderivatives or hexanolderivatives to glucose. Transgenic expression of corresponding genes in plants can be used to influence the biosynthesis of the corresponding glucosides.

The biosynthetic pathway of dhurrin has been studied in otiolated seedlings of *Sorghum bicolor*, and was found to involve two membrane-bound multi-functional cytochrome P450s. The amino acid precursor L-tyrosine is hydroxylated twice by the enzyme CYP79A1 ($P450_{TYR}$) forming (Z)-p-hydroxyphenylacetaldoxime (WO 95/16041), which subsequently is converted by the enzyme CYP71E1 ($P450_{OX}$) to the cyanohydrine p-hydroxymandelonitrile (WO 98/40470). Transgenic expression of said enzymes is used to modify, reconstitute, or newly establish the biosynthetic pathway of cyanogenic glucosides or to modify glucosinolate production in plants.

In dhurrin biosynthesis, the cyanohydrin p-hydroxymandelonitrile forms an equilibrium with p-hydroxyberzaldehyde and CN at physiological pH and is conjugated to glucose by a UDP-glucose:aglycon-glucosyltransferase. Plants have a large capability to glucosylate a wide range of different chemical structures, but the number of glucosyltransferases present in plants and the range of substrate specificities are largely unknown. Earlier studies indicate that both narrow and broad substrate specificities can be found. Unfortunately, the difficulties encountered in isolating glucosyltransferases to homogeneity without a simultaneous loss of their biological activity confuse the picture. The difficulties encountered partly reflect that many glucosyltransferases have similar molecular mass, are labile and present in minute amounts. Whereas over one hundred different cDNAs encoding putative, secondary plant metabolism glucosyltransferases are described in publicly accessible databases, only a few of the proteins have been verified. There are no reports of the isolation of a cyanohydrin glucosyltransferase from a cyanogenic plant. The present invention demonstrates that expression of both the UDP-glucose:mandelonitrile-glucosyltransferase and the enzymes CYP79A1 and CYP71E1 in transgenic plants enables these plants to catalyze the conversion of the amino acid tyrosine to the cyanogenic glucoside dhurrin. Thus, the combined expression of proteins catalyzing the reactions involved in the biosynthesis of cyanogenic glucosides in plants actually establishes the complete pathway for cyanogenic glucoside synthesis in these transgenic plants.

Gene refers to a coding sequence and associated regulatory sequences wherein the coding sequence is transcribed into RNA such as mRNA, rRNA, tRNA, snRNA, double stranded RNA, sense RNA or antisense RNA. Examples of regulatory sequences are promoter sequences, 5' and 3' untranslated sequences and termination sequences. Further elements such as introns may be present as well.

Expression generally refers to the transcription and translation of an endogenous gene or transgene in plants. However, in connection with genes which do not encode a protein such as antisense constructs, the term expression refers to transcription only.

The following solutions are provided by the present invention:

A DNA molecule coding for a UDP-glucose:aglycon-glucosyltransferase conjugating a cyanohydrin (like mandelonitrile, p-hydroxymandelonitrile, acetone cyanohydrine or 2-hydroxy-2-methylbutyronitrile); a terpenoid (like geraniol, nerol or β-citronellol); a phenylderivative (like p-hydroxybenzoic acid, benzoic acid, benzylalcohol, p-hydroxy-benzylalcohol, 2-hydroxy-3-methoxybenzylalcohol, vanillin acid or vanillin) or a hexanolderivative (like 1-hexanol, trans-2-hexen-1-ol, cis-3-hexen-1-ol, 3-methyl-3-hexen-1-ol or 3-methyl-2-hexen-1-ol) to glucose as well as the encoded protein itself;

Said DNA molecule coding for glucosyltransferase having the formula $R_1$-$R_2$-$R_3$, wherein
 $R_1$, $R_2$ and $R_3$ are component sequences consisting of amino acid residues independently selected from the group of the amino acid residues Gly, Ala, Val, Leu, Ile, Phe, Pro, Ser, Thr, Cys, Met, Trp, Tyr, Asn, Gln, Asp, Glu, Lys, Arg and His, and
 $R_2$ consists of 150 or more amino acid residues the sequence of which is at least 50% identical to an aligned component sequence of SEQ ID NO: 1 as determined using the computer program blastp of the BLAST 2.0 set of similarity search programs, optional parameters set to the default values Said DNA molecule, wherein $R_2$ encodes 150–425 amino acid residues such as amino acids 21 to 445, 168 to 448, or 281 to 448 of SEQ ID NO: 1;

Said DNA molecule, wherein $R_1$ and $R_3$ consist independently of 0 to 500 amino acid residues;

Said DNA molecule, wherein $R_1$ or $R_3$ encode one or more additional component sequences having a length of at least 30 amino acids and being at least 65% identical to an aligned component sequence of SEQ ID NO: 1, such as amino acids 21 to 55, 142 to 174, or 303 to 343 of SEQ ID NO: 1;

Said DNA molecule coding for a protein of 300 to 600 amino acid residues length such as defined in SEQ ID NO: 2 or the protein defined in SEQ ID NO: 1;

A method for the isolation of such cDNA molecules;

A method for producing purified recombinant UDP-glucose:aglycon-glucosyltransferase conjugating a cyanohydrin, a terpenoid, a phenylderivative or a hexanolderivative to glucose;

A method for obtaining a transgenic plant as well as the transgenic plant itself comprising stably integrated into its genome DNA coding for said protein or DNA encoding sense RNA, anti sense RNA, double stranded RNA or a ribozyme, the expression of which reduces expression of said protein.

The *Arabidopsis thaliana* genome is expected to contain approximately 120 genes encoding glucosyltransferases involved in natural product synthesis as deduced from the current state of the *Arabidopsis* genome sequencing programme. Other plants are also expected to contain a large number of genes encoding glucosyltransferases. In spite of the presence of numerous glucosyltransferases in *S. bicolor*, none of these except one exert high specificity towards mandelonitrile and p-hydroxymandelonitrile. The presence of several isoforms of this glucosyltransferase is likely considering the evolution and taxonomical background of sorghum and polyploidal forms. The lability of p-hydroxymandelonitrile and the absence of multiple peaks containing p-hydroxymandelonitrile glucosyltransferase activities in *S. bicolor* during column chromatography demonstrate that a specific glucosyltransferase (sbHMNGT) is involved in the biosynthesis of the cyanogenic glucoside dhurrin.

The biosynthesis of cyanogenic glucosides proceeds according to a general pathway, i.e. involving the same type of intermediates in all plants. Accordingly, the enzymes catalyzing these processes in different plant species are expected to show significant similarity. This has already been clearly demonstrated for the part of the pathway involving conversion of amino acids to oximes. This part has in all plants tested been demonstrated to be catalyzed by one or more cytochrome P450 enzymes belonging to the CYP79 family. These cytochromos P450 show more than 40% sequence identity at the amino acid level. The initial conversion of the amino acids to oximes in glucosinolate synthesis is also catalyzed by a cytochrome P450 enzyme belonging to the CYP79 family. In line with these previous findings, it is expected that in plants synthesizing cyanogenic glucosides conjugation of glucose to cyanohydrins follows a conserved biochemical pathway involving structurally related glucosyltransferases. The aim of the present invention is to provide DNA molecules coding for a UDP-glucose:aglycon-glucosyltransferase conjugating a number of cyanohydrins, a terpenoids, phenylderivatives, and hexanolderivatives (p-hydroxybenzoic acid, benzoic acid, benzylalcohol, p-hydroxy-benzylalcohol and/or geraniol)? to glucose and to define their general structure in cyanogenic plants on the basis of the amino acid sequence of the *S. bicolor* UDP-glucose:hydroxymandelonitrile-O-glucosyltransferase and its corresponding gene sequence. Thus the present invention provides DNA molecules coding for a UDP-glucose:aglycon-glucosyltransferase and conjugating a cyanohydrin (like mandelonitrile, p-hydroxymandelonitrile, acetone cyanohydrine or 2-hydroxy-2-methylbutyronitrile); a terpenoid (like geraniol, nerol or β-citronellol); a phenylderivative (like p-hydroxybenzoic acid, benzoic acid, benzylalcohol, p-hydroxy-benzylalcohol, 2-hydroxy-3-methoxybenzylalcohol, vanillic acid or vanillin) or a hexanolderivative (like 1-hexanol, trans-2-hexen-1-ol, cis-3-hexen-1-ol, 3-methyl-3-hexen-1-ol or 3-methyl-2-hexen-1-ol) to glucose having the formula $R_1$-$R_2$-$R_3$, wherein $R_1$, $R_2$ and $R_3$ are component sequences consisting of amino acid residues independently selected from the group of the amino acid residues Gly, Ala, Val, Leu, Ile, Phe, Pro, Ser, Thr, Cys, Met, Trp, Tyr, Asn, Gln, Asp, Glu, Lys, Arg, His and optionally any other amino acid residue which can result from posttranslational modification within a living cell, and $R_2$ consists of 150, preferably 250 or more amino acid residues the sequence of which is at least 50%, preferably at least 55%, or even more prefered at least 70% identical to an aligned component sequence of SEQ ID NO: 1.

Typical amino acid residues which can result from posttranslational modification within a living cell are Aad, bAad, bAla, Abu, 4Abu, Acp, Ahe, Aib, bAib, Apm, Dbu, Des, Dpm, Dpr, EtGly, EtAsn, Hyl, aHyl, 3Hyp, 4Hyp, Ide, alle, MeGly, Melle, MeLys, MeVal, Nva, Nle and Orn.

Typically $R_2$ consists of 150 to 425 amino acid residues, a length of 150 to 280 amino acid residues being preferred. Specific embodiments of R 2 are represented by amino acids 21 to 445, 168 to 448 or 281 to 448 of SEQ ID NO: 1.

R1 and R3 independently consist of 0 to 500, preferably 0 to 350 amino acid residues and may comprise one or more additional component sequences having a length of at least 30 amino acids and being at least 65%, but preferably at least 70% identical to an aligned component sequence of SEQ ID NO: 1. Examples of such additional component sequences are represented by amino acids 21 to 55, 142 to 174 or 303 to 343 of SEQ ID NO: 1. The glycosyltransferases encoded by said DNA molecules generally consist of 300 to 600 amino acid residues, the *S. bicolor* enzyme having a size of 492 amino acid residues as described in SEQ ID NO: 1 and as encoded by SEQ ID NO: 2.

In general there exist two approaches towards sequence alignment. Dynamic programming algorithms as proposed by Needleman and Wunsch and by Sellers align the entire length of two sequences providing a global alingment of the sequences. The Smith-Waterman algorithm on the other hand yields local alignments. A local alignment aligns the pair of regions within the sequences that are most similiar given the choice of scoring matrix and gap penalties. This allows a database search to focus on the most highly conserved regions of the sequences. It also allows similiar domains within sequences to be identified. To speed up alignments using the Smith-Waterman algorithm programs such as BLAST (Basic Local Alignment Search Tool) and FASTA place additional restrictions on the alignments.

Within the context of the present invention overall sequence alignments are conveniently performed using using the program PILEUP available from the Genetic Computer Group, Madison, Wis.

Local alignments are performed conveniently using BLAST, a set of similarity search programs designed to explore all of the available sequence databases regardless of whether the query is protein or DNA. Version BLAST 2.0 (Gapped BLAST) of this search tool has been made publicly available on the internet (currently http://www.ncbi.nim.nih.gov/BLAST/). It uses a heuristic algorithm which seeks local as opposed to global alignments and is therefore able to detect relationships among sequences which share only isolated regions. The scores assigned in a BLAST search have a well-defined statistical interpretation. Particularly useful within the scope of the present invention are the blastp program allowing for the introduction of gaps in the local sequence alignments and the PSI-BLAST program, both programs comparing an amino acid query sequence against a protein sequence database, as well as a blastp variant program allowing local alignment of two sequences only. Said programs are preferably run with optional parameters set to the default values.

Additionally, sequence alignments using BLAST can take into account whether the substitution of one amino acid for another is likely to conserve the physical and chemical properties necessary to maintain the structure and function of a protein or is more likely to disrupt essential structural and functional features. Such sequence similarity is quantified in terms of of a percentage of 'positive' amino acids, as compared to the percentage of identical amino acids and can help assigning a protein to the correct protein family in border-line cases.

Investigations into the quantitative and qualitative substrate specificity of sbHMNGT showed a strong preference for the cyanohydrin present in *S. bicolor*. Thus, in vivo cyanohydrin glucosyltransferases show strong preferences for a limited number of cyanohydrins, terpenoids, phenylderivatives and hexanolderivatives. Nevertheless enzymes catalyzing reactions at the end of biosynthetic pathways often have a broader substrate specificity than those catalyzing preceding reactions resulting in greater flexibility with respect to the evolution of novel secondary metabolite biosynthesis and xenobiotic catabolism. This is illustrated by the finding that whilst the first enzyme of the pathway (CYP79A1) is exclusive for tyrosine, CYP71E1 and sbHMNGT also accept phenylalanine derived oximes and cyanohydrins, respectively. The presence of a nitrile group is also not necessarily required for substrate recognition by sbHMNGT, as demonstrated by the ability of sbHMNGT to glucosylate benzyl alcohol, benzoic acid, vanillic acid, vanillin and 2-hydroxy-3-methoxybenzylalcohol, geraniol, nerof and β-citronellol. The results demonstrate that sbHMNGT accepts substrates which are structurally similar to the mandelonitrile or p-hydroxy-mandelonitrile. This group of substrate compounds also includes Green Note Flavours such as hexan-1-ol, trans-2-hexene-1-ol and cis-3-hexene-1-ol and other tyrosine or phenylalanine related aroma compounds like phenylacetic acid, phenylethylalcohol, and phenylethylacetate (Krings et al, Appl. Microbiol. Biotechnol. 49: 1–8, 1998). The rates observed for glucosylation of benzyl alcohol, benzoic acid and geraniol are lower than those observed for the cyanohydrins. However, they are still high. To this date there are no reports on the isolation or cloning of a monoterpenoid glucosyltransferase nor of glucosyltransferases for hexanol or hexanol derived compounds, despite the obvious importance of these enzyme classes in defining taste and aroma of processed foods and vegetables.

In the process of glycosylation, unstable compounds (aglycons) are generally rendered less chemically reactive and more water soluble through the enzymatic addition of sugar groups. This typically enables the plant to store increased amounts of these aglycons in the form of glycosides. Many of the secondary metabolites synthesised by plants are glycosylated. For instance over 1500 glycosides of flavonoids alone have been characterised. Glycosylation generally occurs as a late or the last step in the biosynthesis of compounds otherwise unstable in the cellular environment, and can provide a pool of inactive and transportable precursor forms of compounds that can be obtained in an active form by hydrolysis with glucosidase enzymes. Conversion of free aglycons such as terpenoids and Green Note Flavours into corresponding glucosides through the introduction of a glucosyltransferase can be used to preserve aroma, flavour and colour components in fruits, vegetables and other plants. The aglycons can be liberated by the action of specific or unspecific b-glusidases during food preparation or consumption. Further optimization of the catalytic properties towards individual desired aroma, flavours or colour compounds may be achieved through directed evaluation or methods of genetic engineering such as gene shuffling or mutation.

For example in the grapevine the glucosylation of many secondary metabolites has recently become the focus of significant research efforts arising from the discovery that many of the aroma, flavour and colour components of wine are derived from grape compounds which occur in large part as glucosides. Among such target compounds are the terpenes, e.g. geraniol which is found in both a free and a glucosylated form. In view of the present invention the glucoside pool of aroma and flavour precursors can be modulated through manipulation of glucosyltransferase activities and aroma and flavour can be released from stored pools of glucosides via acid or enzyme mediated hydrolysis. Thus, in the grape berry and other fruits, vegetables and plants, the introduction of specific glucosyltransferases such as the cloned sbHMGT or reduction of their expression through anti-sense techniques allows directed modification of secondary metabolite composition. This permits modulatation of important free and bound flavour pools of plants allowing the design of fruits, wines and other plant derived products with defined, organoleptic properties.

The ability of a glucosyltransferase to conjugate an aglycon to glucose can for example be determined in an assay comprising the following steps:
a) Incubation of a reaction mixture comprising $^{14}$C-UDP-glucose, aglycon and UDP-glucose:aglycon-glucosyltranslerase at 30° C. between 2 minutes and 2 hours
b) terminating the reaction, and
c) chemical identification and quantification of the glucoside produced.

Typically the reaction mixture has a volume of 5 to 2000 μl, but preferably 20 μl and includes 10–200 mM Tris HCl (pH 7.9); 1–5 μM $^{14}$C-UDP-glucose (about 11.0 GBq mmol$^{-1}$); 0–300 μM UDP-glucose; 0–20 mM aglycone; 25 mM γ-gluconolactone; 0–2 μg/μl BSA and 0–10 ng/μl UDP-glucose:aglycon-glucosyltransferase. β-glucosidase inhibitors other than γ-gluconolactone and protein stabilizers other than BSA may be included as appropriate. One possibility to terminate the reaction is to acidify the reaction mixture for example by adding 1/10 volume of 10% acetic acid.

Chemical identification and quantification of the glucoside formed in the reaction mixture may be achieved using a variety of methodologies including NMR spectroscopy, TLC analysis, HPLC analyses or GLC analysis in proper combinations with mass spectrometric analysis of the glucoside.

Reaction mixtures for analysis by NMR spectroscopy usually have a total volume of 0.5–1 ml, are incubated for 2 hours and include 0–10 mM aglycon, e.g. 2 mM p-hydroxy-mandelonitrile or 6.5 mM geraniol, 3 mM UDP-glucose, 2.5 μg recombinant sbHMNGT, and 0.5 mg BSA. Glucosides are extracted for example with ethyl acetate and lyophillized prior to NMR analysis.

For TLC analysis the reaction mixtures are applied to Silica Gel 60 F254 plates (Merck), dried and eluted in a solvent such as ethyl acetate:acetone:dichloromethane: methanol: $H_2O$ (40:30:12:10:8, v/v). Plates are dried for one hour at room temperature and exposed to storage phosphorlmaging plates prior to scanning on a PhosphorImager. Based on the specific radioactivity of the radiolabelled UDP-glucose, the amount of glucoside formed is quantified.

The radioactivity may also be determined by liquid scintillation counting (LSC analysis). In some cases, where the glucoside formed is derived from a very hydrophobic aglycon, e.g. mandelonitrile, the glucoside can be extracted into an ethyl acetate phase and thereby be separated from unincorporated $^{14}$C-UDP-glucose. 2 ml of scintillation cocktail are added to 250 μl of each ethyl acetate extract and analyzed using a liquid scintillation counter. During column fractionation, those fractions containing sbHMNGT activity can be identified using mandelonitrile as the aglycon substrate and ethyl acetate extraction of the glucoside formed.

Knowledge of SEQ ID NO: 1 and SEQ ID NO: 2 can be used to accelerate the isolation and production of DNA molecules coding for a UDP-glucose:aglycon-glucosyltransferase conjugating cyanohydrins, terpenoids, phenyl-derivatives or hexanolderivatives to glucose which method comprises (a) preparing a cDNA library from plant tissue expressing UDP-glucose:aglycon-glucosyltransferase,
(b) using at least one oligonucleotide designed on the basis of SEQ ID NO: 2 or SEQ ID NO: 1 to amplify part of the UDP-glucose:aglycon-glucosyltransferase cDNA from the cDNA library,
(c) optionally using one or more oligonucleotides designed on the basis of SEQ ID NO: 2 or SEQ ID NO: 1 to amplify part of the UDP-glucose:aglycon-glucosyltransferase cDNA from the cDNA library in a nested PCR reaction, (d) using the DNA obtained in steps (b) or (c) as a probe to screen the DNA library prepared from plant tissue expressing UDP-glucose:aglycon-glucosyltransferase, and (e) identifying and purifying vector DNA comprising an open reading frame encoding a protein characterized by an amino acid component sequence of at least 150 amino acid residues length having 50% or more sequence identity to an aligned component sequence of SEQ ID NO: 2, and (f) optionally further processing the purified DNA to achieve, for example, heterologous expression of the protein in a microorganism like *Escherichia coli* or *Pichia pastoris* for subsequent isolation of the glucosyltransferase, determination of its substrate specificity and generation of an antibody.

In process steps (b) and (c) the second oligonucleotide used for amplification is preferably an oligonucleotide complementary to a region within in the vector DNA used for preparing the cDNA library. However, a second oligonucleotide designed on the basis of the sequence of SEQ ID NO: 2 or SEQ ID NO: 1 can also be used. A prefered embodiment of this method for the isolation of cDNA is described in Example 4. cDNA clones coding for UDP-glucose:aglycon-glucosyltransferase or fragments of this clone may also be used on DNA chips alone or in combination with the cDNA clones encoding proteins belonging to the CYP79 or CYP71E1 family of proteins or fragments of these clones. This provides an easy way to monitor the induction or repression of cyanogenic glucoside synthesis in plants as a result of biotic and abiotic factors.

A further embodiment of the present invention are UDP-glucose:aglycon-glucosyl-transferases conjugating a cyanohydrin to glucose such as the *S. bicolor* enzyme conjugating p-hydroxymandelonitrile to glucose.

Purified recombinant UDP-glucose:aglycon-glucosyltransferases can be obtained by a method comprising dye chromatography and elution with UDP-glucose. An appropriate column material for dye chromatography is Reactive Yellow 3 preferably cross-linked on beaded agarose. Elution of the protein is conveniently achieved using 2 mM UDP-glucose.

The present invention also provides nucleic acid compounds comprising an open reading frame encoding the novel proteins according to the present invention. Said compounds are characterized by the formula $R_A\text{-}R_B\text{-}R_C$, wherein $R_A$, $R_B$ and $R_C$ constitute component sequences consisting of nucleotide residues independently selected from the group of the nucleotide residues G, A, T and C or the group of nucleotide residues G, A, U and C, $R_A$ and $R_C$ consist independently of 0 to 1500, preferably 0 to 1050 nucleotide residues;

$R_B$ consists of 450–1260 and preferably 450–840 nucleotide residues; and the component sequence $R_B$ is at least 65% identical to an aligned component sequence of SEQ ID NO: 2.

Specific examples of the component sequence $R_B$ are represented by nucleotides 61 to 1335, 502 to 1344, or 841 to 1344 of SEQ ID NO: 2.

In a preferrred embodiment of the present invention at least one of the component sequences $R_A$ or $R_C$ comprises one or more additional component sequences which have a length of at least 150 nucleotide residues and are at least 60% identical to an aligned component sequence of SEQ ID NO: 2. Specific examples of such additional component sequences are represented by nucleotides 61 to 165, 427 to 522, or 907 to 1029 of SEQ ID NO: 2.

The pathway for dhurrin synthesis can be introduced into acyanogenic plants by expression of CYP79A1, CYP71E1 and the sbHMNGT. These three gene products derived from the same plant species, i.e. sorghum, assemble as a macromolecular complex resulting in stronger channeling of the intermediates in the pathway and less free intermediates are released into the plant.

Expressed as transgenes the DNA molecules encoding glycosyltransferases according to the present invention are particularly useful to modify the biosynthesis of cyanogenic glucosides in plants. When the gene encoding a UDP-glucose:cyanohydrin glucosyltransferase is expressed in conjunction with genes encoding cytochrome P450 enzymes belonging to the CYP79 family (catalyzing the conversion of an amino acid to the corresponding N-hydroxyamino acid and the oxime derived from this N-hydroxy amino acid or a cytochrome P450 monooxygenase) and CYP71E family (catalyzing the conversion of an aldoxime to a nitrile and the conversion of said nitrile to the corresponding cyano hydrin), acyanogenic wild-type plants are converted into cyanogenic plants. Proper selection of promoters to provide constitutive, inducible or tissue specific expression of the genes provides means to obtain transgenic cyanogenic plants with desired disease and herbivor responses. Likewise, the content of cyanogenic glucosides in cyanogenic plants may be modified or reduced using anti-sense, double stranded RNA (dsRNA) or ribozyme technology using the same genes. Cyanogenic glucosides belong to the group of phytoanticipins. In cyanogenic plants, blockage or reduction of UDP-glucose:cyanohydrin glucosyltransferase activity is expected to result in production and accumulation of the same products as normally produced by degradation of cyanogenic glucosides in damaged or infected plant cells. Thus using anti-sense or ribozyme technology, plants can be obtained that produce the degradation products of cyanogenic glucosides in the same tissues where cyanogenic glucosides are produced in the wild-type plant resulting in plants with an altered resistance to pathogens and herbivors. Thus, it is a further aspect of the present invention to provide transgenic plants comprising stably integrated into the genome DNA coding for a UDP-glucose:aglycon-glucosyltransferase conjugating cyanohydrins, terpenoids, phenylderivatives or hexanolderivatives to glucose or DNA encoding sense RNA, anti sense RNA, double stranded RNA or a ribozyme, the expression of which reduces expression of a UDP-glucose:aglycon-glucosyltransferase conjugating p-hydroxymandelonitrile to glucose. Such plants can be produced by a method comprising (a) introducing into a plant cell or tissue which can be regenerated to a complete plant, DNA comprising a gene expressible in that plant encoding a UDP-glucose:aglycon-glucosyltransferase conjugating cyanohydrins, terpenoids, phenylderivatives or hexanoldorivatives to glucose or DNA encoding sense RNA, anti sense RNA or a ribozyme, the expression of which reduces the expression of a UDP-glucose:aglycon-glucosyltransferase conjugating a cyanohydrin to glucose; and (b) selecting transgenic plants.

EXAMPLES

Example 1

UDP-glucose:p-hydroxymandelonitrile-glucosyltransferase assay

Generally a 20 µl reaction mixture including
100 mM Tris HCl (pH 7.9),
1–5 µM $^{14}$C-UDP-glucose (11.0 GBq mmol$^{-1}$, Amersham LIFE SCIENCE),
0–300 µM UDP-glucose,
0–20 mM p-hydroxymandelonitrile (dissolved in water, freshly prepared),
25 mM γ-gluconolactone,
0–1 mg BSA and
0.5–10 µl of protein preparation, is incubated at 30° C. between 2 minutes and 2 hours. Thereafter the reaction is terminated by the addition of ⅒ of the reaction volume of 10% acetic acid. The same assay conditions are used to determine the glucosylation of mandelonitrile, benzoic acid, benzylalcohol, geraniol and a number of other aglycons.

To determine the substrate specificity of recombinant sbHMNGT incubation lasts for 20 min at 30° C. and the general protocol above is adapted to include
1.25 mM aglycone (dissolved in ethanol except for flavonoids which are dissolved in ethylene glycol monoether),
1.25 µM $^{14}$C-UDP-glucose,
12.5 µM UDP-glucose,
100 ng recombinant sbHMNGT, and
4 µg BSA.

Quantitative determination of the activity of recombinant sbHMNGT is carried out using 4 minutes incubation at 30° C. Analyses are carried out as for the determination of substrate specificity except that the reaction mixtures are composed as folows:
1, 5 or 10 mM aglycone,
5 µM $^{14}$C-UDP-glucose,
0.2 mM UDP-glucose,
200 ng recombinant sbHMNGT, and
24 µg BSA.

Reaction mixtures for analysis by NMR spectroscopy are incubated for 2 hours in a total volume of 0.5–1 ml including
2 mM p-hydroxymandelonitrile or 6.5 mM geraniol,
3 mM UDP-glucose,
2.5 µg recombinant sbHMNGT, and
0.5 mg BSA.

Glucosides are extracted with ethyl acetate and lyophillized using speedy-vac prior to NMR analysis.

For TLC analysis the reaction mixture is applied to Silica Gel 60 F254 plates (Merck), dried and eluted in a solvent containing ethyl acetate:acetone:dichloromethane:methanol:$H_2$ (40:30:12:10:8, v/v). Plates are dried for one hour at room temperature and exposed to storage phosphorlmaging plates (Molecular Dynamics) prior to scanning on a Storm 860 Phosphorimager (Molecular Dynamics).

For analysis by liquid scintillation counting (LSC) reaction mixtures are extracted with 400 µl of ethyl acetate to separate glucosides from unincorporated $^{14}$C-UDP-glucose. 2 ml of Ecoscint A (National Diagnostics, New Jersey, USA) are added to 250 µl of each ethyl acetate extract and analyzed using a Win Spectral 1414 (Wallac) liquid scintillation counter. Mandelonitrile is used as substrate to assay fractions generated by liquid chromatography.

Example 2

Purification of UDP-glucose:p-hydroxymandelonitrile-glucosyltransferase

Except where indicated all steps are carried out at 4° C. Although the endogenous substrate of sbHMNGT is p-hydroxymandelonitrile, mandelonitrile is employed as the substrate for the assay of sbHMNGT activity throughout purification, since it is an equally good substrate. Furthermore, the absence of a hydroxyl group at the para-position of the benzene ring rules out the possibility of p-glucosyloxymandelonitrile synthesis, which would be indistinguishable from dhurrin using the LSC assay.

1 kg of S. bicolor seeds are soaked in water over night at room temperature and subsequently grown for 2 days at 30° C. in darkness as described in (Halkier et al, Plant Physiol. 90: 1552–1559, 1989). Seedling shoots are harvested and extracted in 2 volumes of ice-cold extraction buffer (250 mM sucrose; 100 mM Tris HCl (pH 7.5); 50 mM NaCl; 2 mM EDTA; 5% (w/v) of polyvinylpolypyrrolidone; 200 µM phenylmethylsulfonyl fluoride; 6 mM DTT) using mortar and pestle. The extract is filtered through a nylon mesh prior to centrifugation at 20,000×g for 20 min. The supernatant fraction is subjected to differential ammonium sulphate fractionation (35–70%) with 1 hour precipitations and centrifugations at 20,000×g for 20 min. The pellet is resuspended in buffer A (20 mM Tris HCl (pH 7.5); 5 mM DTT) using a paint brush and desalted using a 100 ml Sephadex G-25 (Pharmacia) or Biogel P-6 (Bio-Rad) column (20 ml/min flow-rate) equilibrated in buffer A. Whilst these purification steps do not result in a measurable increase of the specific activity of sbHMNGT, low molecular weight solutes (including cyanide-precursors) are effectively removed. The first UV-absorbing peak is collected and applied to a 20 ml Q-sepharose (Pharmacia) column (60–80 ml/hr flow-rate) equilibrated in buffer B (buffer A+50 mM NaCl). The column is washed with buffer B until the baseline has stabilised and proteins are eluted with a linear gradient from 50 to 400 mM NaCl in buffer A (800 ml total). 10 ml fractions are collected and 3–5 µl assayed for mandelonitrile glucosyltransferase activity by LSC. All sbHMNGT activity bound to O-sepharose is eluted between 150–200 mM NaCl with a -7-fold purification. Combined active fractions are diluted five-fold in buffer B and concentrated 20-fold using an Amicon YM30 or YM10 membrane prior to storage at −80° C.

The remaining steps of the dye chromatography purification are carried out at room temperature or at 4° C. One quarter of combined concentrated ion-exchange fractions (~10–15 mg protein in 5 ml) is applied to a column (1 cm×10 cm) containing Reactive Yellow 3 cross-linked on 4% beaded agarose (Lot 63H9502; Sigma) equilibrated in buffer B (10–15 ml/hr). The column is washed with buffer B until the baseline has stabilised. Proteins are eluted with 10 ml of 2 mM UDP-glucose in buffer B. Active fractions containing essentially pure sbHMNGT are pooled and stored at −80° C. with or without addition of 1 mg/ml BSA.

Results: Initial experiments indicated that a 2-day germination period was optimal with regards to total sbHMNGT activity, protein concentration and extract volume. The use of a Waring blender resulted in less than 50% of the activity as compared to extraction with mortar and pestle. sbHMNGT activity was largely unaffected by freezing at −80° C. and the addition of glycerol had no effect. The addition of elevated concentrations of DTT in buffer solutions (5 mM compared to 2 mM) resulted in a ten-fold greater activity after storage at 4° C. for 2 days. This pronounced effect of DTT was primarily found in crude preparations, wheras partially purified ion-exchange preparations were less responsive to the concentration of reducing agents.

Several pseudoaffinity reagents were tested out in minicolumn format including Cibachron blue 3G, Reactive Green 19, Reactive Yellow 3 and UDP-glucuronic acid cross-linked with 4% beaded agarose. Trials with elution using NaCl and UDP-glucose at varying salt concentrations identified Reactive Yellow 3 as the superior column material. sbHMNGT activity binds to the Reactive Yellow 3 at 50 mM NaCl and could be eluted after washing with a slight increase in NaCl concentration, without any measurable UV absorbance in the eluate. sbHMNGT activity binds at either salt concentration and can be eluted after washing with a slight increase in NaCl concentration, without any measurable UV-absorbance in the eluate. sbHMNGT activity correlates with a polypeptide migrating around 50–55 kDa by SDS-PAGE, although there are several impurities present (data not shown). Elution with 2 mM UDP-glucose instead of NaCl results in the elution of a similarly migrating polypeptide in apparent homogeneity. When the protocol is repeated it was found that a low column height in relation to total protein was crucial in order to obtain the same degree of purity. Assuming that all of the polypeptide which was visualised by SDS-PAGE was active (and therefore that all inactive protein had been lost) and compensating for cold substrate dilution (UDP-glucose), sbHMNGT represented approximately 0.25% of total protein and was purified 420-fold with a yield of 22%.

Example 3

Peptide Generation and Sequencing

Approximately 5 μg of sbHMNGT is subjected to N-terminal sequencing using a protein sequencer (mode! G1000A, Hewlett-Packard). For peptide digestion, approximately 100 μg of sbHMNGT are precipitated with trichloracetic acid and resuspended in 50 μl of 50 mM Tris.HCl (pH 8.0), 5 mM DTT and 6.4 M Urea. The preparation is incubated at 60° C. for 50 min, cooled to room temperature, and diluted with 3 volumes of 30 mM Tris (pH 7.7) and 1.25 mM EDTA. Endo Lys-C (Promega) is added at a 1:25 ratio (w/w) and the reaction mixture is allowed to incubate for 24 hours at 37° C. Peptides are purified by reverse-phase HPLC using a Vydac 208TP52 C8 column (250 mm×21 mm) and Beckman System Gold HPLC equipment. Peptides are applied at a 0.2 m/min flow-rate in buffer C (0.1% trifluoroacetic acid) and eluted with a linear gradient from 0 to 80% acetonitrile in buffer C. Fractions are collected manually and sequenced as described above.

Example 4

Cloning

PCR amplification: 1st round PCR amplification reactions are carried out using 2 units of Taq DNA polymerase (Pharmacia), 4 μl of 10×Taq DNA polymerase buffer, 5% (v/v) dimethyl sulfoxide, 1 μl dNTPs (10 mM), 80 pmoles each of primers C2EF (5'-TTYGTIWS-ICAYTGYGGITG-GAA-3', SEQ ID NO: 3) and T7 (5'-AATACGACTCAC-TATAG-3', SEQ ID NO: 4) and about 10 ng of plasmid DNA template in a total volume of 40 μl. The plasmid DNA template is prepared from a unidirectional pcDNAII (Invitrogen) plasmid library made from 1–2 cm high etiolated *S. bicolor* seedlings (Bak et al, Plant Mol. Biol. 36: 393–405, 1998). Thermal cycling parameters are 95° C., 5 min, 3×(95° C. for 5 sec, 42° C. for 30 sec, 72° C. for 30 sec), 32×(95° C. for 5 sec, 50° C. for 30 sec, 72° C. for 30 sec) and a final 72° C. for 5 min.

2nd round PCR amplifications are carried out as above, except for using primers C2DF (5'-GARGCIACIGCIGCIG-GICARCC-3', SEQ ID NO: 5) and T7, and 1 μl of 1st round reaction as DNA template. Thermal cycling parameters are 95° C., 5 min, 32×(95° C. for 5 sec, 55° C. for 30 sec, 72° C. for 30 sec) and a final 72° C. for 5 min. The PCR reaction mixtures are subjected to gel electrophoresis using a 1.5% agarose gel and an approximately 600 bp band is excised and cleaned using a Qiaex II gel extraction kit (Qiagen). The cleaned PCR product is then ligated into the pGEM-T vector and used to transform the *E coli* JM109 strain according to the manufacturers instructions (Promega). Nucleic acid sequencing reveals the presence of two previously obtained peptide sequences in the translation product of PCR clone 15#44.

Cloning and Library Screening: The PCR clone 15#44 is used as a template for generating a 306 bp digoxigenin-11-dUTP-labelled probe by PCR using primers 441 F (5'-GAGGCGA-CGGCGGCGGGGCAG-3', SEQ ID NO: 6) and 442R (5'-CATGTCACTGCTTGCCCCCGACCA-3', SEQ ID NO: 7) according to the manufacturer's instructions (Boehringer Mannheim). The labelled probe is cleaned using the Qiaex II gel extraction kit after gel electrophoresis with a 1.5% agarose gel and employed to screen approximately 50,000 colonies of the abovementioned plasmid library. Hybridizations are carried out over night at 65° C. in 5×SSC, 0.1% (w/v) N-lauroylsarcosine, 0.02% (w/v) SDS and 1% blocking reagent (Boehringer Mannheim). Membranes are then washed in 0.5×SSC at 60° C., 3×15 min. Seven hybridizing clones are isolated and one full-length clone, sbHMNGT1, is chosen for further characterization.

Example 5

Identity and Similarity Between sbHMNGT and Translation Products of Known or Putative glucosyltransferase-Encoding cDNAs Table 1 summarizes the overall identity respectively similarity between sbHMNGT and known or putatice glycosyltransferase amino acid sequences as well as the identities respectively similarities in the corresponding N-terminal regions, i.e. the region defined as the sequence N-terminal of the consensus sequence xCLxWL with the split-point being at amino acid residue 291/292 of sbHMNGT.

Table 2 summarizes the similarity respectively identity between the amino acid sequence of sbHMNGT region α, defined as residues 188–229 in HMNGT, and corresponding sequences in known or putative glycosyltransferase amino acid sequences.

The calculations of similarity and identity are based on a pairwise comparisons of cDNA translation products using the GAP program (Genetic Computer Group, Madison, Wis.), wherein A/G, Y/F, S/T, V/I/L, R/K/H, and D/E/N/Q are considered to constitute similar residues. Abbreviated sequence names are stSGT (*Solanum tuberosum* solanidine-glucosyltransforase: GenBank™ accession number U82367); bnTHGT (*Brassica napus* thiohydroximate-S-glucosyltransferase: SEQ ID NO: 28 of EP-771 878-A1), zmUFGT (Maize flavonoid-glucosyltransferase: GenBank™ accession number X13502), vvUFGT (*Vitis vinifera* anthocyanidin-glucosyltransferase: GenBank™ accession number AF000371), psGT (*Pisum sativum* UDP-glucuronosyltransferase: GenBank™ accession number AF034743), meGT (Cassava UTP-glucose glucosyltransferase: GenBank™ accession number X77464), and zmIAAGT (Maize Indole-3-acetate beta-glucosyltransferase: GenBank™ accession number L34847).

TABLE 1

| | sbHMNGT | | | |
|---|---|---|---|---|
| | Overall % | | N-terminal % | |
| | Identity | Similarity | Identity | Similarity |
| zmUFGT | 36.7 | 41.5 | 32.6 | 37.1 |
| vvUFGT | 30.0 | 38.7 | 23.8 | 33.3 |
| psGT | 41.6 | 51.5 | 32.9 | 46.3 |
| meGT | 31.3 | 41.6 | 25.3 | 36.8 |
| zmIAAGT | 34.9 | 41.3 | 27.8 | 35.0 |
| snSGT | 28.9 | 38.0 | 23.6 | 31.0 |
| bnTHGT | 30.7 | 38.0 | 24.7 | 33.3 |

TABLE 2

| α region identities (italic) and similarities (bold face) | | | | | |
|---|---|---|---|---|---|
| | sbHMNGT | psGT | zmUFGT | vvUFGT | mhGT |
| sbHMNGT | | *45.2%* | *26.2%* | *19.1%* | *20%* |
| psGT | 69.1% | | — | — | — |
| zmUFGT | 35.7% | — | | *47.6%* | *37.5%* |
| vvUFGT | 35.7% | — | 59.5% | | — |
| mhGT | 37.5% | — | 55.0% | — | |

Example 6

Heterologous Expression

Primers EXF1 (5'-AATAAAAAGCATATGGGAAG-CAACGCGCCGCCTCCG-3', SEQ ID NO: 8) and EXR1 (5-TTGGATCCTCACTGCTTGCCCCCGACCA-3', SEQ ID NO: 9) are used to amplify a 1500 bp full-length sbHMNGT insert by PCR, using the sbHMNGT1 plasmid as template. The primers contain 5' recognition sites for restriction endonucleases NdeI (EXF1) and BamHI (EXR1). PCR reaction conditions are essentially as described in example 4, except for the thermal cycling parameters which are 95° C., 3 min, 30×(95° C. for 5 sec, 53° C. for 30 sec, 72° C. for 90 sec) and a final 72° C. for 5 min. The PCR product is gel purified, digested with NdeI and BamHI, gel purified once again and ligated into the plasmid expression vector pSP19g10L (Barnes, Methods in Enzymology 272: 3–14, 1996) which has also been digested with the restriction enzymes NdeI and BamHI and gel purified. The ligation reaction mixture is then used to transform *E. coli* JM109 cells according to the manufacturers instructions (Promega). Alter selection of successfully cloned cells, expression is initiated as described in (Ford et al, J. Biol. Chem. 273: 9224–9233, 1998). Briefly, 600 µl of a 37° C. over night culture are added to 300 ml luria broth (LB) containing 100 µg/ml ampicillin. The culture is allowed to grow at 28° C. under continuous shaking at 150 rpm for 5 hours and IPTG is then added to a final concentration of 0.4 mM. After induction the culture is allowed to continue growing over night and harvested by centrifugation at 2500×g for 10 min. The pellet is resuspended in 9 ml of 200 mM Tris pH 7.9, 1 mM EDTA, 5 mM DTT and 0.1 mg/ml lysozyme. An equal volume of ice-cold water is added and the mixture allowed to incubate for 10 min at RT, followed by 20 min incubation on ice. After the addition of 18 µmoles of phenylmethylsulfonyl fluoride and 100 units of DNaseI/ml (Sigma), the suspension is subjected to three freeze and thaw cycles at −20° C. Phenylmethylsulfonyl fluoride is adjusted to 1.5 mM final concentration and the preparation centrifuged at 15,000×g for 15 min. Negative controls, containing no insert in the plasmid vector, are prepared as above. For purification of the recombinant protein two 300 ml cultures are lysed as above and further purified as for the native protein. Briefly, crude cell lysate is subjected to Q-sepahrose chromatography, desalting and Reactive Yellow 3 chromatography as described in example 2. The yield of recombinant protein is approximately 1 mg/100 ml LB culture.

Example 7

Substrate Specificity of Recombinant sbHMNGT Compared to Desalted Crude Etiolated *Sorghum* Seedling Extract Glucosyltransferase activity was determined by TLC using $^{14}$C-UDP-glucose. Filled boxes in Table 1 below (■) indicate that a radiolabelled product was visualised after incubation with the respective aglycone substrate. Empty boxes (□) indicate that no radiolablled products could be detected under the experimental conditions employed. Figures in brackets indicate the relative $V_{max}$ for each aglycon with calculated standard deviations. The $V_{max}$ value for p-hydroxymandelonitrile was 1500 mol of product/mol of sbHMNGT/sec.

TABLE 3

| | ACTIVITY | |
|---|---|---|
| SUBSTRATES cyanohydrins | Crude Sorghum extract | Recombinant sbHMNGT |
| 1) mandelonitrile | ■ | ■ (77.8 ± 8.6%) |
| 2) p-hydroxymandelonitrile | ■ | ■ (100 ± 7.2%) |
| 3) acetone cyanohydrin | □ | □ |
| benzyl derivatives | | |
| 4) hydroquinone | ■ | □ |
| 5) benzyl alcohol | ■ | ■ (13.1 ± 2.1%) |
| 6) p-hydroxybenzyl alcohol | ■ | ■ |
| 7) benzoic acid | ■ | ■ (4.2 ± 0.8%) |
| 8) p-hydroxybenzoic acid | ■ | □ |
| 9) p-hydroxybenzaldehyde | ■ | □ |
| 10) gentisic acid | □ | □ |
| 11) caffeic acid | ■ | □ |
| 12) 2-hydroxy cinnamic acid | ■ | □ |
| 13) resveratrol (stilbene) | ■ | □ |
| 14) salicylic acid | ■ | □ |
| 15) p-hydroxymandelic acid | ■ | □ |
| 16) vanillic acid | ■ | ■ |
| 17) vanillin | ■ | ■ |
| 18) 2-hydroxy-3-methoxybenzlalcohol | ■ | ■ |
| flavonoids | | |
| 19) quercetin (flavonol) | ■ | □ |
| 20) cyanidin (anthocyanidin) | ■ | □ |
| 21) biochanin A (isoflavone) | ■ | □ |
| 22) naringenin (flavanone) | ■ | □ |
| 23) apigenin (flavone) | ■ | □ |
| hexanol derivatives | | |
| 24) 1-hexanol | ■ | ■ |
| 25) trans-2-hexen-1-ol | ■ | ■ |
| 26) cis-3-hexen-1-ol | ■ | ■ |
| 27) 3-methyl-3-hexen-1-ol | ■ | ■ |
| 28) 3-methyl-2-hexen-1-ol | ■ | ■ |
| others | | |
| 29) indole acetic acid (plant hormone) | ■ | □ |
| 30) geraniol (monoterpenoid) | ■ | ■ (11.0 ± 0.5%) |

TABLE 3-continued

| | ACTIVITY | |
|---|---|---|
| SUBSTRATES cyanohydrins | Crude Sorghum extract | Recombinant sbHMNGT |
| 31) tomatidine (alkaloid) | ■ | □ |
| 32) nerol | ■ | ■ |
| 33) p-citronellol | ■ | ■ |

---

The invention claimed is:

1. An isolated DNA molecule comprising a nucleotide sequence coding for a UDP-glucose:aglycon-glucosyltransferase that conjugates an aglycon selected from the group consisting of a cyanohydrin, a terpenoid, a benzyl derivative and a hexanol derivative to glucose, wherein the compliment of said nucleotide sequence hybridizes to SEQ ID NO:2 under the following hybridization conditions: hybridization in 5×SSC, 0.1% N-lauroylsarcosine, 0.02% SDS, 1% Blocking Reagent at 65° C., and washing three times for 15 minutes in 0.5×SSC at 60° C.

2. The isolated DNA molecule according to claim 1, wherein said aglycon is selected from the group consisting of mandelonitrile, p-hydroxymandelonitrile, gerinol, nerol, β-citronellol, benzoic acid, benzylalcohol, p-hydroxy-benzylalcohol, 2-hydroxy-3-methoxybenzylalchol, vanillic acid, vanillin, 1-hexenol, trans-2-hexen-1-ol, cis-3-hexen-1-ol, 3-methyl-3-hexen-1-ol and 3-methyl-2-hexen-1-ol.

3. The isolated DNA molecule according to claim 1, wherein the polypeptide encoded by said nucleotide sequence comprises amino acids 21 to 445, 168 to 448, or 281 to 448 of SEQ ID NO: 1.

4. The isolated DNA molecule according to claim 1, wherein said nucleotide sequence codes for a UDP-glucose:aglycon-glucosyltransferase of 300 to 600 amino acid residues in length.

5. The isolated DNA molecule according to claim 1, wherein said nucleotide sequence codes for a UDP-glucose:aglycon-glucosyltransferase comprising the amino acid sequence set forth in SEQ ID NO: 1.

6. The isolated DNA molecule according to claim 1, comprising the nucleotide sequence set forth in SEQ ID NO: 2.

7. A method for the isolation of a cDNA molecule comprising a nucleotide sequence that codes for a UDP-glucose:aglycon-glucosyltransferase that conjugates a cyanohydrin, a terpenoid, a benzyl derivative or a hexanolderivative to glucose; comprising (a) preparing a cDNA library from plant tissue expressing said UDP-glucose:aglycon-glucosyltransferase, (b) [designing at least one oligonucleotide to bind to SEQ ID NO: 2, (c) optionally designing further a oligonucleotide to bind to SEQ ID NO: 2, (d)] PCR amplifying part of a UDP-glucose:aglycon-glucosyltransferase cDNA from the cDNA library using the oligonucleotides of SEQ ID NO: 3 and SEQ ID NO: 5 [oligonucleotide from steps (b) and (c)], (c) screening said cDNA library prepared from plant tissue expressing UDP-glucose:aglycon-glucosyltransferase using the PCR amplified DNA generated by step (b)

(d) identifying and purifying vector DNA isolated in step (c), and [comprising an open reading frame encoding a protein characterized by an amino acid component sequence of at least 150 amino acid residues in length having 50% or more sequence identity to a sequence of at least 150 amino acids residues of SEQ ID NO: 1, and (g) sequencing the open reading frame of the DNA to confirm its identity]

(e) assaying heterologously expressed protein encoded by the isolated cDNA of step (d) for glucosyltransferase activity; wherein the isolated cDNA comprises a nucleotide sequence that codes for a polypeptide having UDP-glucose:aglycon-glucosyltrasferase activity that conjugates a cyanohydrin, a terpenoid, a benzyl derivative or a hexanol derivative to glucose.

8. The isolated DNA molecule according to claim 1, wherein said nucleotide sequence is isolated from a plant that produces a cyanogenic glucoside.

9. The isolated DNA molecule according to claim 8, wherein the cyanogenic glucoside is dhurrin.

10. The isolated DNA molecule according to claim 8, wherein said plant is selected from the group consisting of the genera *Sorghum, Triticum, Secale*, and *Macadamia*.

11. The isolated DNA molecule according to claim 8, wherein said plant is selected from the group consisting of the species *Sorghum bicolor, Triticum aestivum, Secale cereale*, and *Macadamia ternifolia*.

12. The isolated DNA molecule according to claim 8, wherein said plant is *Sorghum bicolor*.

13. A recombinant nucleic acid construct comprising a promoter operatively linked to the DNA molecule according to claim 1.

14. A transgenic host cell comprising the recombinant nucleic acid construct of claim 13.

15. The transgenic host cell according to claim 14, which is a bacterial cell or a plant cell.

\* \* \* \* \*